US00PP10793P

United States Patent [19]

Fleming et al.

[11] Patent Number: Plant 10,793

[45] Date of Patent: Feb. 16, 1999

[54] HIBISCUS PLANT NAMED 'KOPPER KING'

[76] Inventors: David W Fleming; James R Fleming, both of 8101 S. 14th St., Lincoln, Nebr. 68512

[21] Appl. No.: 963,542

[22] Filed: Nov. 3, 1997

[51] Int. Cl.[6] ..... A01H 5/00

[52] U.S. Cl. ..... Plt./67.8

[58] Field of Search ..... Plt./67.8

*Primary Examiner*—Howard J. Locker

[57] ABSTRACT

A new and distinct cultivar of winter hardy Hibiscus plant named 'Kopper King' is the result of a unique hybridization. This new and distinct cultivar is characterized primarily as to novelty by its extreme cold hardiness to Zone 4, its vibrant reddish-copper colored "maple-cut" leaves, its large white flowers with bright red centers and red streaking to the petal edges, its vigorous and uniform growth habit, and its floriferous nature from midsummer until frost.

5 Drawing Sheets

BACKGROUND OF THE NEW PLANT

The new plant of this invention is the result of a unique hybridization, with the breeding achievement being evidenced in the outstanding combination of characteristics exhibited by this new and distinct hibiscus plant, which include:

(a) Refined and uniquely colored 3 to 5 lobed leaves with a "maple-cut" which have relatively smooth margins and an evenly distributed reddish-copper coloration that compliments the landscape;
(b) Large flowers that are outstanding for their white, thick-textured petals with bright red centers surrounded by hot pink coloring, which streaks through the venation, to the edges of the petals;
(c) The plant being very floriferous with flowers that stay open one full day;
(d) The plant being medium-sized, but vigorous, with compact and uniform breaking action which gives it unique landscape utility; and
(e) The plant being so hardy it can consistently withstand winter temperatures of at least −30 degrees Fahrenheit.

SUMMARY OF THE INVENTION

'Kopper King' was the result of a 40 year breeding program. Its ancestry includes *Hibiscus moscheutos, Hibiscus coccineus*, and *Hibiscus militaris*. More specifically, the plant resulted from backcrossing and inbred seedling of 'Dahliatown Orchid' (not patented), a *Hibiscus moscheutos* cultivar, with 'Jazzmen' (not patented) a hybrid of *Hibiscus coccineus, Hibiscus moscheutos*, and *Hibiscus militaris*, for three generations.

This new plant first bloomed in the summer of 1987 and was selected by David and James Fleming on their property in Lincoln, Nebr. Asexual propagation of the plant by cuttings and by root division in Lincoln, Nebr., has shown that the unique and distinguishing features of the plant are faithfully transmitted from generation to generation and appear to be firmly fixed.

Since its origin, the plant has bloomed from midsummer until frost, while exhibiting the above mentioned distinctive characteristics. This hardy hibiscus plant contributes to the market with its sheer beauty, its compact growth habit, it great resistance to disease and insects, its stability through extremes in rain and drought, and its extreme hardiness.

BRIEF DESCRIPTION OF THE DRAWINGS

The flower, bud, foliage, and growth habit of the plant are shown in the attached illustrations.

More specifically, Sheet 1 shows the bloom, buds in varying stages of maturity, and the foliage.

Sheet 2 is a close up view of the flower.

Sheet 3 depicts the growth habit of the cultivar.

Sheet 4 shows the buds and foliage in greater detail.

Sheet 5 is a close up view of the foliage, and also shows buds. The colors illustrated are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE number designations are in accordance with the *Dictionary of Color* (Maerz and Paul), while general color recitations are consistent with ordinary American color terminology. 'Kopper King' has not been observed under all possible environmental conditions. It is to be understood that the phenotype may vary significantly with variations in environment such as temperature, light intensity, and day length, without, however any difference in the genotype of the plant. The following botanical characteristics and observations are taken from the plant when grown under normal outdoor conditions in Lincoln, Neb.

The Plant

Parentage:

*Seed parent*.—'Jazzmen' (hybrid of *Hibiscus moscheutos, Hibiscus coccineus*, and *Hibiscus militaris*).

*Pollen parent*.—Inbreed seedling of 'Dahliatown Orchid' (*Hibiscus moscheutos*).

Origin: A selected seedling of from the stated cross.
Type of plant: Hardy; Herbaceous perennial.
Classification: Hybrid Hibiscus plant.
Propagation: Relatively easy to propagate; holds its distinguishing characteristics through successive propagations by cuttings and divisions.
Size: About 31–42 inches tall; about 24–30 inches wide.
Form: Symmetrical; annual growth from perennial roots.
Habit: Upright and uniformly branched.
Growth: Vigorous; compact.
Hardiness: Hardy to at least −30 degrees Fahrenheit.

General health: Plant is very disease resistant; very pest resistant.

Propagation: Relatively easy; fast rooting.

Foliage:

1. *Arrangement*.—Alternate.
2. *Shape*.—Juvenile — variable, ovate to 3-lobed palmate leaf. Mature — refined, palmate 3 to 5 lobed leaf with relatively smooth margins with some serrations, acute apices.
3. *Size*.—Mature leaf — (petiole base to apex) length is about 6½ inches (16.5 cm), width is about 5 inches (13 cm).
4. *Color*.—Young leaves (upper side) — slightly brighter than Indian Red, L-5, page 39, PLATE 8; background green L-8, page 65, PLATE 21. Mature leaves (upper side) — Burgundy L-8, page 135, PLATE 56; background green I-7, page 67, PLATE 22. Veins — K-1, page 115, PLATE 46. Underside of leaves — J-1, page 135, PLATE 56 and J-6, page 67, PLATE 22.
5. *Surface texture*.—Glabrous (to semi-glabrous on lower leaves).
6. *Petiole length*.—About 2½ inches (5.5 cm).
7. *Petiole color*.—Slightly brighter than K-1, page 115, PLATE 46.

Stems: The stems are stout at the base, becoming more slender toward the apices; coloration is consistent with the petiole.

The Flower

Blooming period: Profuse from July until frost.

Flower diameter: Large; about 8 inches (20.5 cm) to 12 inches (30cm).

Borne: Singly in leaf axils, from midpoint of stems upward.

Bloom duration: Individual bloom lasts one full day.

Form: Flat; petals very overlapping.

Bud:

1. *Length*.—About 1½ inches (4 cm), on day before opening.
2. *Color*.—A-7, page 27, PLATE 2.
3. *Duration*.—One to two weeks.

Corolla:

1. *Petal character and dimensions*.—Flat and very overlapping. Length is about 4 inches (10 cm). Width is about 4 inches (10 cm).
2. *Coloration*.—White with red center or eye (about 2½ inches in diameter) and red streaking extending outward from eye to edge of petals. (a) White petals — A-7, page 27, PLATE 2. (b) Venation in petals — K-6, page 31, PLATE 4. (c) Eye zone — H-11, page 135 PLATE 56 (inner), and E-6, page 33, PLATE 5 (outer).
3. *Texture*.—Smooth.
4. *Substance*.—Medium thick.
5. *Shape*.—Flat and very overlapping.

Reproductive organs:

1. *Staminal column*.—Stamen along basal two-thirds. Stamen length — About 1½ inches (4 cm). Stamen color — A-1, page 25, PLATE 1. Pollen color — H-1, page 41, PLATE 9.
2. *Style*.—Terminates upper one-third of Staminal column. Stigmatic lobe color — G-1, page 41, PLATE 9.

Calyx: Connate at the base; about 2 inches (5 cm) in length.

Stipules: None.

Epicalyx: Whorl of bracts.

1. *Shape*.—7–10 slender, sword-shaped bractlets.
2. *Length*.—About 1½ inches (4 cm).
3. *Color*.—K-8, page 61, PLATE 19; tips J-1, page 133, PLATE 55.

Peduncle:

1. *Length*.—About 1½ inch (4 cm).
2. *Strength*.—Stiff and sturdy.

General Observations

This plant, as a hybridized hardy Hibiscus, is valuable to the landscape market for its improvements in thicker textured and uniquely colored flowers, refined "maple-cut" reddish-copper colored foliage, all around vigor, good breaking action, and adaptation to extreme environments, including the ability to consistently survive winter temperatures of at least −30 degrees Fahrenheit.

We claim:

1. A new and distinct cultivar of Hibiscus plant, as herein shown and described, characterized by its bold reddish-copper "maple-cut" foliage, its large white flowers with red center and red streaking to the petal edges, its vigor, and its hardiness.

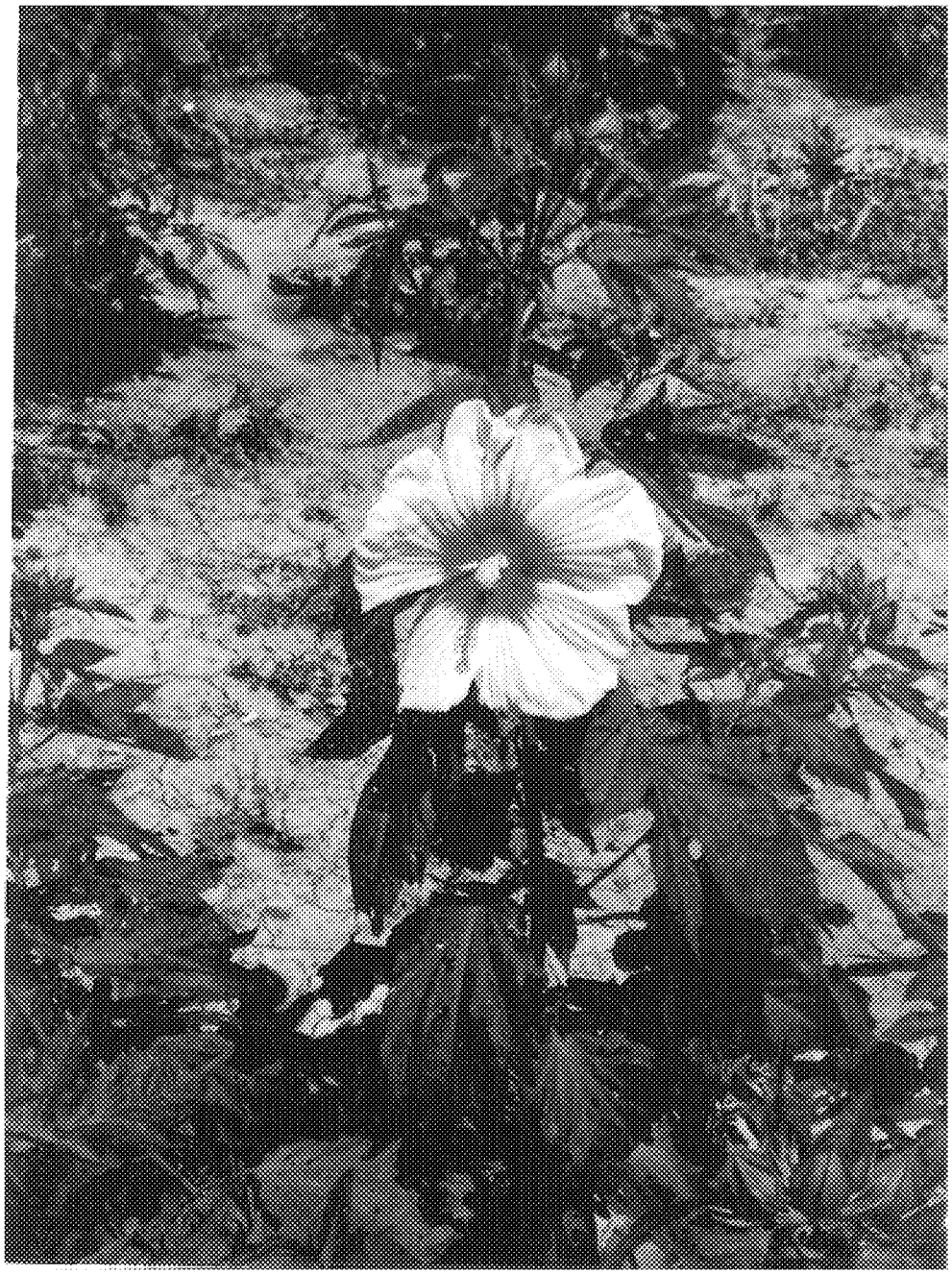

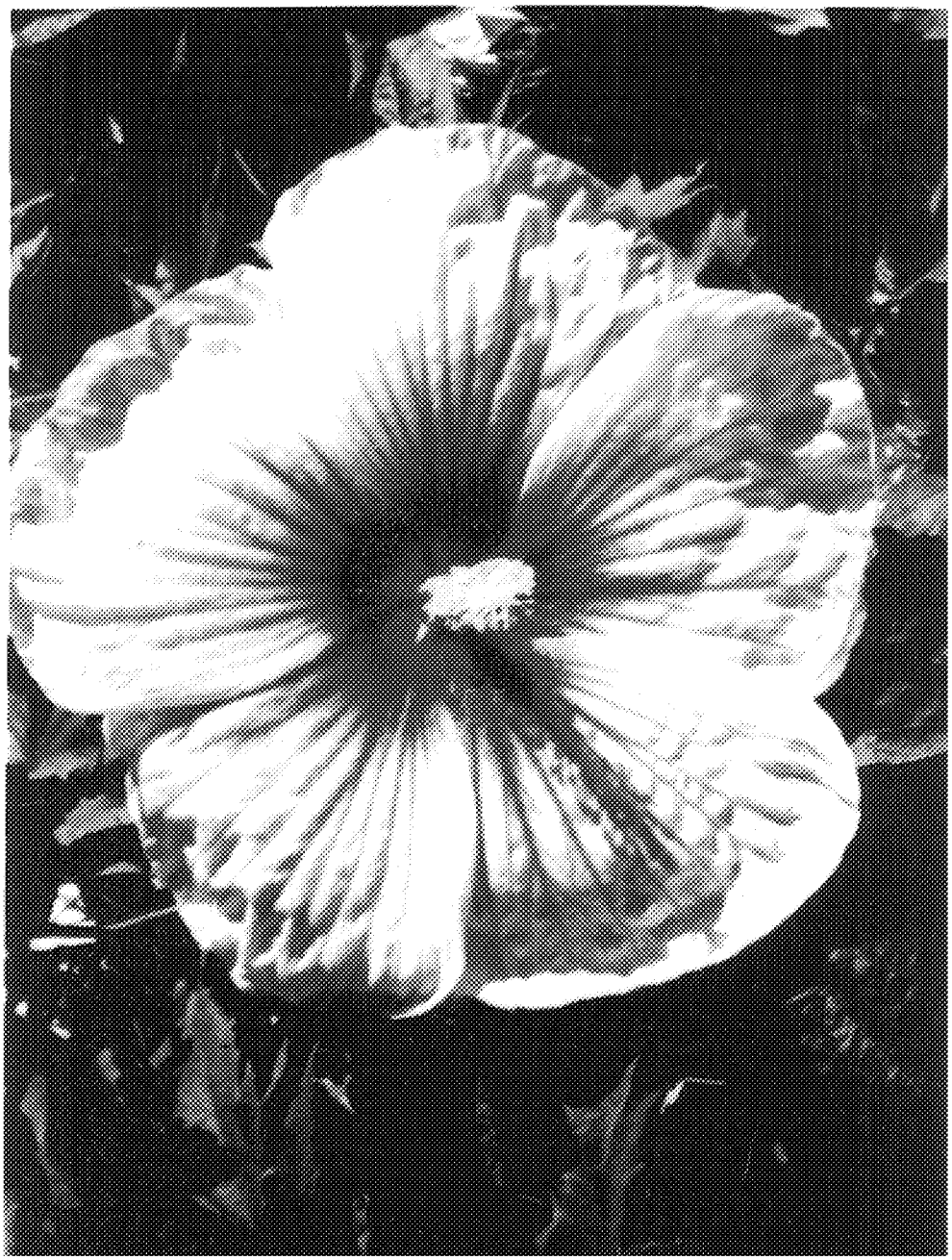

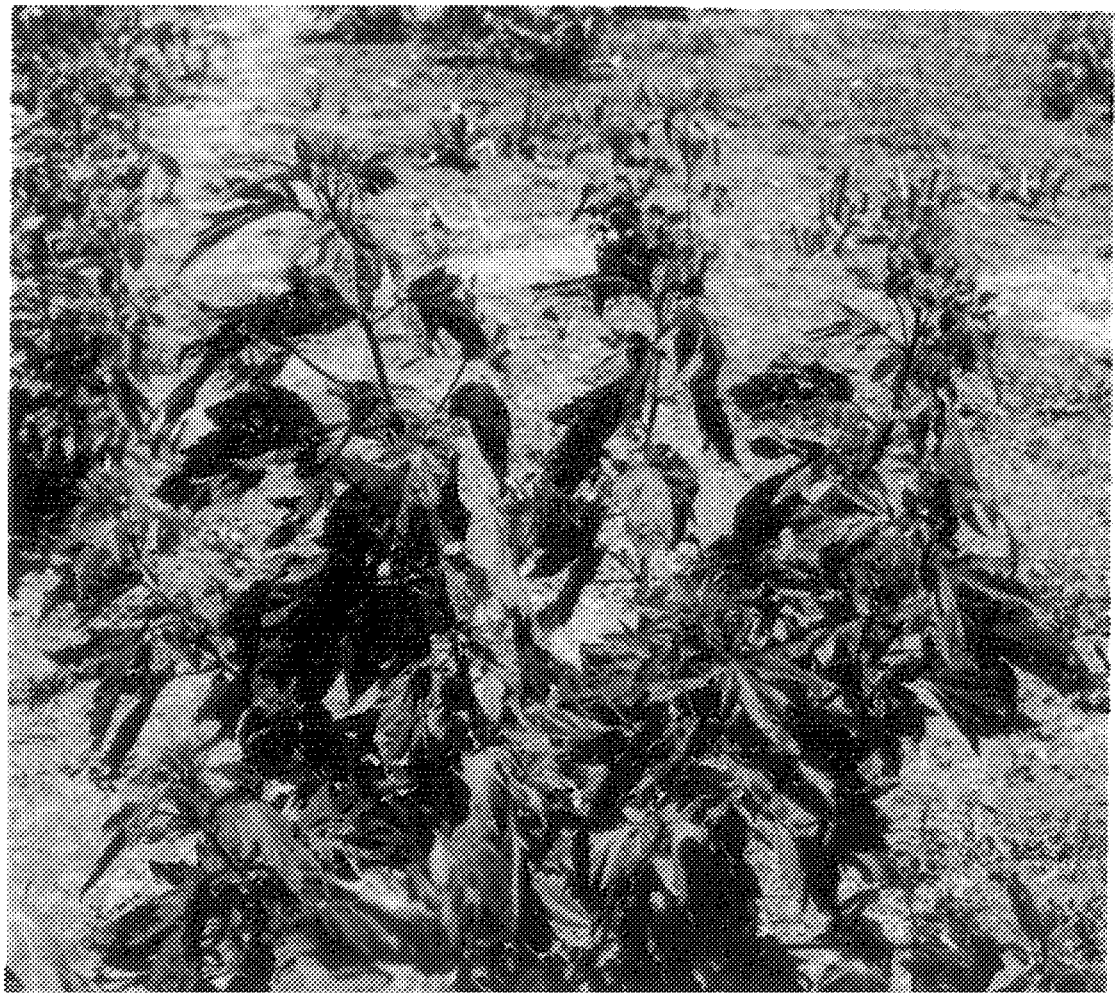

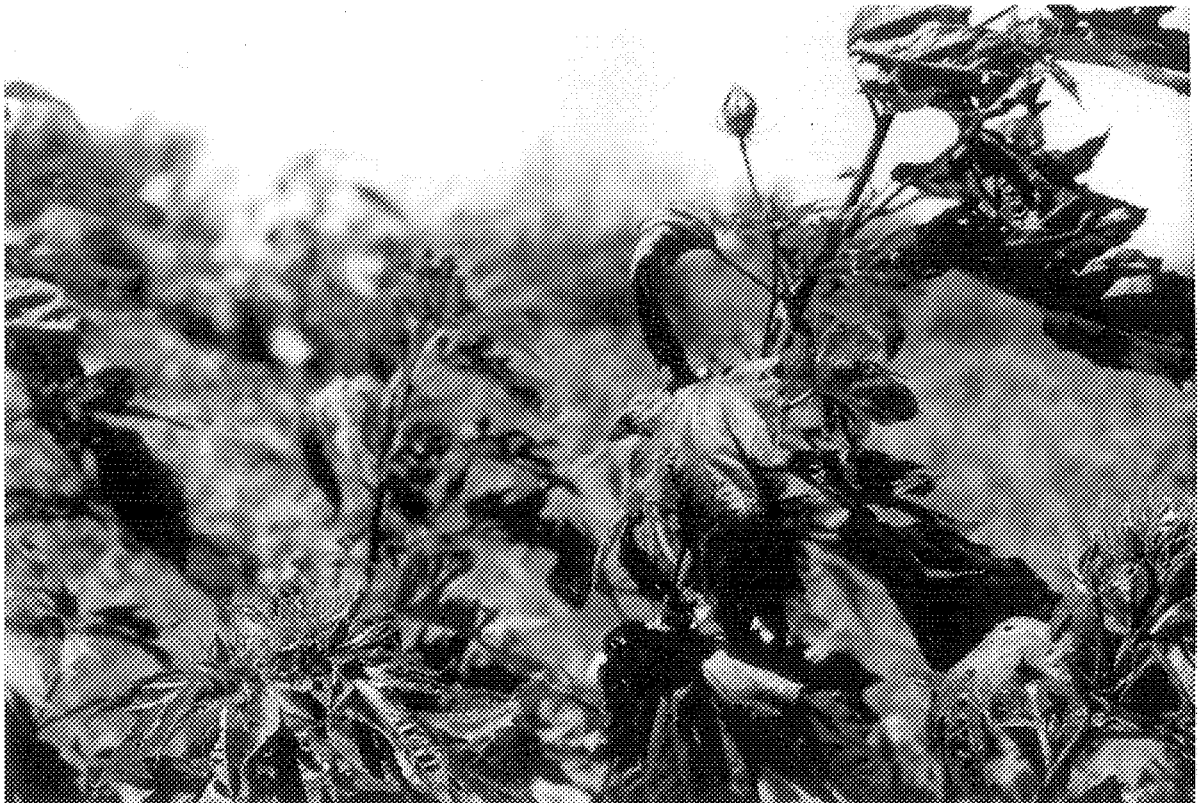

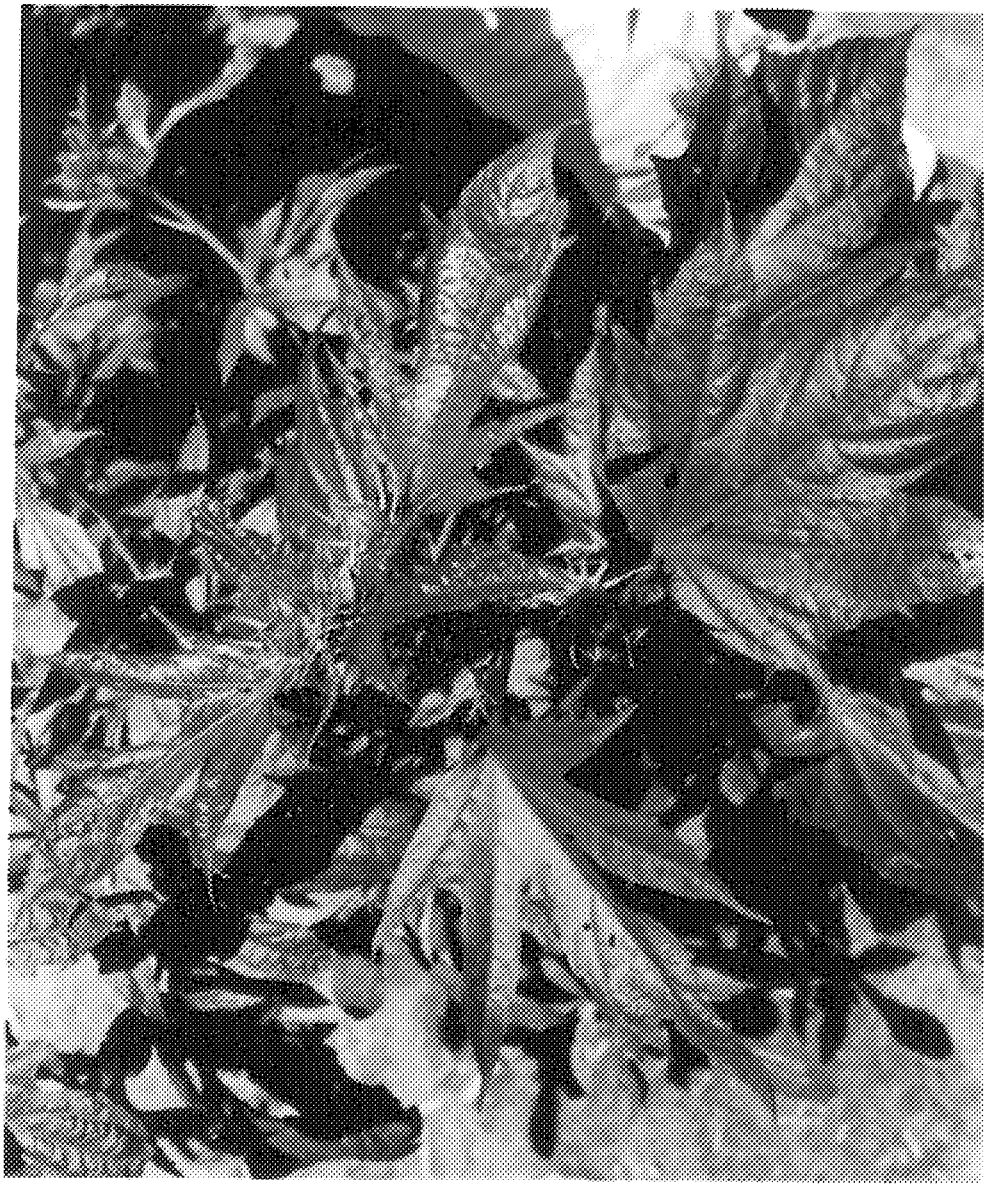

* * * * *